United States Patent
Mravik et al.

(10) Patent No.: US 8,877,799 B2
(45) Date of Patent: Nov. 4, 2014

(54) INORGANIC SALT COMPLEXES OF VILDAGLIPTIN

(75) Inventors: Andras Mravik, Budapest (HU); Imre Koehegyi, Budapest (HU); Laszlo Pongo, Kerepes (HU); Balazs Volk, Budapest (HU); Gabor Nemeth, Budapest (HU); Jozsef Barkoczy, Budapest (HU); Kalman Nagy, Budapest (HU); Gyoergy Ruzsics, Budapest (HU); Judit Broda, Budapest (HU); Andras Dancso, Budapest (HU); Adrienn Keszthelyi, Budapest (HU); Jozsef Debreczeni, Budapest (HU)

(73) Assignee: Egis Gyogyszergynar Nyilvanosan Muekoedoe Reszvenytarsasag, Budapest (HU)

( * ) Notice: Subject to any disclaimer, the term of this patent is extended or adjusted under 35 U.S.C. 154(b) by 207 days.

(21) Appl. No.: 13/500,356

(22) PCT Filed: Oct. 7, 2010

(86) PCT No.: PCT/HU2010/000106
§ 371 (c)(1),
(2), (4) Date: Sep. 11, 2012

(87) PCT Pub. No.: WO2011/042765
PCT Pub. Date: Apr. 14, 2011

(65) Prior Publication Data
US 2013/0005790 A1    Jan. 3, 2013

(30) Foreign Application Priority Data
Oct. 7, 2009   (HU) ...................................... 0900638

(51) Int. Cl.
*C07D 207/16*   (2006.01)

(52) U.S. Cl.
CPC .................................... *C07D 207/16* (2013.01)
USPC .......................................... 514/423; 548/528

(58) Field of Classification Search
None
See application file for complete search history.

(56) References Cited

U.S. PATENT DOCUMENTS

| 7,375,238 | B2 | 5/2008 | Schaefer |
| 2008/0167479 | A1 | 7/2008 | Winter |
| 2008/0279932 | A1 | 11/2008 | Reber |

FOREIGN PATENT DOCUMENTS

| WO | WO 2007/019255 | * | 2/2007 | ........... C07D 207/16 |

* cited by examiner

*Primary Examiner* — Alicia L Otton
(74) *Attorney, Agent, or Firm* — Lucas & Mercanti, LLP; Jonathan Myers (57) ABSTRACT

The present invention relates to the use of novel vildagliptin complexes for the manufacture of high purity vildagliptin of Formula I and/or pharmaceutical acceptable salts thereof. Further objects of the present invention are pharmaceutically acceptable complexes of vildagliptin and/or amorphous and crystalline forms, anhydrous forms, amorphous and crystalline hydrates, amorphous and crystalline solvates of the complexes and a process for the preparation thereof. Another object of the present invention is the high purity vildagliptin and pharmaceutically acceptable salts thereof prepared form the vildagliptin complexes of the present invention, a process for the preparation thereof and pharmaceutical compositions containing vildagliptin base, pharmaceutically acceptable salts and/or complexes and use thereof for the treatment of type 2 diabetes (NIDDM). The present invention provides pharmaceutically advantageous high purity vildagliptin complexes.

30 Claims, 8 Drawing Sheets

Figure 1: The X-ray powder diffraction pattern of vildagliptin magnesium(II)-chloride complex (2:1)

Figure 2: The X-ray powder diffraction pattern of vildagliptin calcium(II)-chloride trihydrate complex (1:1:3)

Figure 3: The X-ray powder diffraction pattern of vildagliptin zinc(II)-chloride complex (2:1)

Figure 4: The X-ray powder diffraction pattern of vildagliptin zinc(II)-chloride complex (1:1)

Figure 5: The X-ray powder diffraction pattern of vildagliptin copper (II)-chloride complex (1:1)

Figure 6: The X-ray powder diffraction pattern of zinc(II)-bromide complex (1:1)

Figure 7: The X-ray powder diffraction pattern of zinc(II)-acetate complex (1:1)

Figure 8: The X-ray powder diffraction pattern of vildagliptin stroncium(II)-nitrate complex (1:1)

US 8,877,799 B2

INORGANIC SALT COMPLEXES OF VILDAGLIPTIN

CROSS REFERENCE TO RELATED APPLICATIONS

This application is the US National Phase of PCT/HU2010/000106 filed 7 Oct. 2010 and claiming the benefit of the priority of Hungarian Patent Application P 0900638 filed 7 Oct. 2009.

FIELD OF THE INVENTION

The present invention relates to the use of novel vildagliptin complexes for the manufacture of high purity vildagliptin of Formula I and/or pharmaceutical acceptable salts thereof. Further objects of the present invention are pharmaceutically acceptable complexes of vildagliptin and/or amorphous and crystalline forms, anhydrous forms, amorphous and crystalline hydrates, amorphous and crystalline solvates of the complexes and a process for the preparation thereof. Another object of the present invention is the high purity vildagliptin and pharmaceutically acceptable salts thereof prepared form the vildagliptin complexes of the present invention, a process for the preparation thereof and pharmaceutical compositions containing vildagliptin base, pharmaceutically acceptable salts and/or complexes and use thereof for the treatment of type 2 diabetes (NIDDM). The present invention provides pharmaceutically advantageous high purity vildagliptin complexes.

TECHNICAL BACKGROUND OF THE INVENTION

1-[2-(3-hydroxyadamant-1-yl-amino)acetyl]pyrrolidin-(2S)-carbonitrile of the formula (I)

(INN: vildagliptin) is used for the treatment of type 2 diabetes (non-insulin dependent). It is known that dipeptidile peptidase IV (DPP-IV) inhibitors are effective in the treatment of diseases which are mediated by DPP-IV. DPP-IV inhibits glucagon-like peptide-1 (GLP-1), which is one of the main stimulants of insulin secretion of pancreas. Moreover GLP-1 positively influences glucose transformation. Therefore inhibition of DPP-IV is effective in the treatment of diseases such as non-insulin dependent diabetes mellitus (NIDDM).

1-[2-(3-hydroxyadamant-1-yl-amino)acetyl]pyrrolidin-(2S)-carbonitrile of formula I (vildagliptin) and the pharmaceutically acceptable salts thereof are described first in EP 1 137 635 A1. Vildagliptin base and some analogues therefore are described in EP 1 137 635 A1 and pharmaceutical acceptable acid addition salts thereof are generally mentioned in the specification.

WO 2007/019255 international patent application describes pharmaceutically acceptable acid addition salts of vildagliptin. Five of the salts, such as hydrochloride, hydrogen sulphate (two polymorphs) hydrogen fumarate, hydrogen malonate are characterised by physical and spectral data.

It is known, that the solubility and bioavailability of the bases are not always sufficient. Therefore the stabilization by salt formation could be a useful solution.

According to WO 2007019255 the salts of vildagliptin—stored in solid form or in the organism—are more stable than the vildagliptin base of formula I. The salts are more soluble in water, therefore they have potentially better bioavailability. According to the description of WO 2007019255 the salts are not hygroscopic and have advantageous formulation properties. The application compares the stability of the vildagliptin base, hydrochloride and hydrogen fumarate salts mixed with several excipients under different conditions. According to the results the stability of the salts is better than that of the base in powder mixture. In pages 44 to 45 of WO 2007019255 it is described that vildagliptin base almost completely decomposes in water until three days and only 7.5% active ingredient is detectable after tree days contrary to the salts.

Physical and chemical properties and spectral data of vildagliptin polymorphisms are not known.

SUMMARY OF THE INVENTION

An object of the present invention is the use of the 1-[2-(3-hydroxyadamant-1-yl-amino)acetyl]pyrrolidin-(2S)-carbonitrile (vildagliptin) complexes of the general formulae II and III for the preparation of high purity vildagliptin of the formula I and/or pharmaceutically acceptable salts thereof.

An other object of the present invention is 1-[2-(3-hydroxyadamant-1-yl-amino)acetyl]pyrrolidin-(2S)-carbonitrile (vildagliptin) complexes of the general Formula (II)

wherein
M stands for an alkali metal, alkaline earth metal or transitional metal cation
A stands for an organic or inorganic anion
n is 1 or 2
x and y stand for 1, 2 or 3
and amorphous or crystalline forms thereof.

Further object of the invention are [2-(3-hydroxyadamant-1-yl-amino)acetyl]pyrrolidin-(2S)-carbonitrile (vildagliptin) complexes containing stoichiometric or non-stoichiometric amount of water of the Formula (III)

wherein
M stands for an alkali metal, alkaline earth metal or transitional metal cation
A stands for an organic or inorganic anion n is 1 or 2 x and y stands for 1, 2 or 3 z stands for a number between 0.5 to 4.

and amorphous or crystalline forms thereof.

Another object of the present invention is high purity vildagliptin base of the formula I, which is manufactured by using (vildagliptin) complexes of the general formulae II and III. The invention further relates to the high purity vildagliptin salts of the general formula (IV)

wherein

'B' stands for a pharmaceutically acceptable organic or inorganic acid anion. The high purity vildagliptin salts of the formula IV can be prepared by using high purity vildagliptin base of the present invention and/or directly by using the (vildagliptin) complexes of the general formulae II and III.

The present invention relates to processes for producing vildagliptin complexes of the general formulae II and III, processes for producing high purity vildagliptin base of the formula I, which is manufactured by using (vildagliptin) complexes of the general formulae II and III, and a process for preparing the high purity vildagliptin salts of the general formula IV, wherein B stands for a pharmaceutically acceptable organic or inorganic acid anion, by using high purity vildagliptin base of the present invention and/or directly by using the (vildagliptin) complexes of the general formulae II and III.

A further object of the present invention is a composition containing vildagliptin complexes of the general formulae II and III, high purity vildagliptin of formula I and/or pharmaceutically acceptable salts thereof according to the present invention, processes for preparing such compositions, and the use of vildagliptin complexes of the general formula II and/or III and/or vildagliptin of the formula I and/or pharmaceutically acceptable salts thereof for the treatment of type 2 diabetes (NIDDM).

DETAILED DESCRIPTION OF THE INVENTION

An object of the present invention is the use of the 1-[2-(3-hydroxyadamant-1-yl-amino)acetyl]pyrrolidin-(2S)-carbonitrile (vildagliptin) complexes of the general formulae II and III for the preparation of high purity vildagliptin of the formula I and/or pharmaceutically acceptable salts thereof.

An other object of the present invention is 1-[2-(3-hydroxyadamant-1-yl-amino)acetyl]pyrrolidin-(2S)-carbonitrile (vildagliptin) complexes of the general Formula II, wherein M stands for an alkali metal, alkaline earth metal or transitional metal cation A stands for an organic or inorganic anion n is 1 or 2 x and y stand for 1, 2 or 3 and amorphous or crystalline forms thereof.

Further object of the invention are [2-(3-hydroxyadamant-1-yl-amino)acetyl]pyrrolidin-(2S)-carbonitrile (vildagliptin) complexes containing stoichiometric or non-stoichiometric amount of water of the Formula III, wherein M stands for an alkali metal, alkaline earth metal or transitional metal cation A stands for an organic or inorganic anion n is 1 or 2 x and y stands for 1, 2 or 3 z stands for a number between 0.5 to 4.

and amorphous or crystalline forms thereof.

Another object of the present invention is high purity vildagliptin base of the formula I, which is manufactured by using (vildagliptin) complexes of the general formulae II and III. The invention further relates to the high purity vildagliptin salts of the general formula IV, wherein 'B' stands for a pharmaceutically acceptable organic or inorganic acid anion.

The high purity vildagliptin salts of the formula IV can be prepared by using high purity vildagliptin base of the present invention and/or directly by using the (vildagliptin) complexes of the general formulae II and III The present invention relates to processes for producing vildagliptin complexes of the general formulae II and III, processes for producing high purity vildagliptin base of the formula I, which is manufactured by using (vildagliptin) complexes of the general formulae II and III, and a process for preparing the high purity vildagliptin salts of the general formula IV, wherein B stands for a pharmaceutically acceptable organic or inorganic acid anion, by using high purity vildagliptin base of the present invention and/or directly by using the (vildagliptin) complexes of the general formulae II and III.

A further object of the present invention is a composition containing vildagliptin complexes of the general formulae II and III, high purity vildagliptin of formula I and/or pharmaceutically acceptable salts thereof according to the present invention, processes for preparing such compositions, and the use of vildagliptin complexes of the general formula II and/or III and/or vildagliptin of the formula I and/or pharmaceutically acceptable salts thereof for the treatment of type 2 diabetes (NIDDM).

In the present specification 'transition metal' stands for metals belonging to the $3^{rd}$ to $12^{th}$ groups of the periodic table, such as the elements of zinc-group.

A marketed pharmaceutical composition has to meet several, regulatory authority requirements, and should be supported by documentation. One part of the requirements relates to the pharmaceutical composition, the other part of the requirements relates to the pharmaceutically active ingredient, which requirements are in close closely linked.

The vildagliptin base is produced by reacting 3-aminoadamantane-1-ol of the formula (V)

and 1-(2-chloroacetyl)-pyrrolidine-(2S)-carbonitrile of the formula

Therefore this intermediate compounds are constant impurities of the vildagliptin synthesis. A further impurity of the coupling reaction is the twice alkylated (2S,2'S)-1,1'-{[(3-hydroxytricyclo[3.3.1.1$^{3,7}$]dec-1-il)imino]bis(1-oxoethan-2,1-diyl)}dipyrrolidine-2-carbonitrile of the formula According to our experiments the formulation of the impurities can not be avoided, only the amount of the impurities can be decreased by optimization of the reaction conditions.

The aim of WO 2008084383 is the minimization of the amount of the component of the formula VII. According to the examples 8 to 23 the ratio of the vildagliptin base to the impurity of the formula VII was 40:1 even after optimization, in other words more than 2% of the impurity of the formula VII was present in the rude product of the reaction. According to example 1 in case of purification by recrystallization form ethyl methyl ketone, —which turns out to be the best way of purification—the ratio of the vildagliptin base to the impurity of the formula VII does not exceeded 99.7:0.30, i.e. the amount of the impurity of the formula VII is 0.3%. The allowable amount of the known impurities in an pharmaceutical active ingredient can not exceed 0.15% according to the pharmaceutical requirements (ICH guideline). This amount of the impurity could exceed only if the safety of the composition is supported by supplementary toxicological investigations. Therefore not even the compound with the highest purity according to WO 2008084383 fulfils the requirements of the ICH guideline in spite of the optimization of the coupling reaction and the further recrystallization It is noteworthy that the 3-amino-adamantane-1-ol of the formula V, which is one of the intermediate compounds being a constant impurity of the vildagliptin synthesis and does not contains UV-active groups. No method for the qualitative and quantitative determination of this impurity is known. Therefore the impurity of the formula V is probably not detected by HPLC measurement of vildagliptin purity. Only one method is described in connection with the detection of the compound of the formula V, which is mass spectrometry (MS) coupled with HPLC but this method is not used for quantitative determination in pharmaceutical industry.

It has been surprisingly found that at reacting vildagliptin base of the formula I with salts of alkali metals, alkaline earth metals or transition metals in solution the complexes of the general formulae II and III are formed.

The complexes are completely different from the acid addition salts of vildagliptin regarding the composition and chemical characteristics thereof which differences can be seen on comparing the compounds of the general formulae II and III with acid addition salts of the compounds of general the formula IV. The acid addition salts are positively charged on the basic nitrogen and an ionic bond is between the salt and the negatively charged anion. On the other hand the cation is connected by a coordinate covalent bond or noncovalent bond to the groups of the vildagliptin, which are disposed to form complexes (—C≡N, —C=O, —NH—, —OH). Therefore the formula of the complexes is completely different from that of the salts.

It has been surprisingly found that in spite of the secondary bonds the complexes are not only solid forms but the melting point of some complexes is higher than that of the vildagliptin base or salts. The stochiometry of the complexes is well characterised and stable, and does not alter during purification by recrystallization. According to the thermo gravimetrics (TG) experiments on warming the complexes to their melting point, they do not decompose.

According to our experiments the vildagliptin complexes can be produced by a simple, reproducible and environmentally friendly process feasible in industrial scale with excellent purity. The high purity is due to the surprising fact that the impurities of the formulae VI and VII of vildagliptin do not form complexes under the same conditions thus the impurities can be removed from the active ingredient. This finding is supported by the following experiment. We tried to form complexes with the compounds of formulae VI and VII. Under the conditions of example 3, the compounds of formulae VI and VII did not form solid complexes. Therefore the complex formation is an excellent method for purifying vildagliptin base and it is more effective than the methods known from the state of the art.

An HPLC method based on light scattering is developed by us for the detection of the UV-inactive compound of the formula V. According to our experiments after the coupling reaction vildagliptin of the formula I always contains said impurity of the formula V, the amount of the impurity being 4 to 5% in the crude product. However in the complexes or in the base which is produced form the complexes the amount of the impurity of the formula V was under the detectable amount (0.03%).

The calcium chloride trihydrate complex of vildagliptin [compound of the general formula III, wherein M denotes calcium(II) ion, A stands for chloride ion, n is 1, x is 1, y is 2 and z is 3] according to example 2 has the following properties:

HPLC purity (UV and light scattering method)>99.97% [<0.03% (VII), <0.03% (V), <0.03% (VI)].

Enantiomer purity: (chiral HPLC, UV detection): >99.9%.

The object of the present invention is the complexes of vildagliptin formed by salts of alkali metals, alkaline earth metals and transition metals according to the general formula II and the hydrates of such complexes according to the general formula III. These complexes have higher purity, advantageous pharmaceutical properties and are more stable than the vildagliptin base and salts produced by the known processes.

The cations of the salts used by complex formation are selected from lithium(I), sodium(I), potassium(I), or caesium (I) ion, alkaline earth metal ions such as magnesium(II), calcium(II), or strontium(II) ion; cations of transition metals, such as zinc(II), copper(II), nickel(II), cobalt(II), ferri(III) or manganese(II) ion. Preferably magnesium(II), calcium(II), strontium(II), zinc(II) or copper(II) cation can be used. Fluoride, chloride, bromide, iodide, nitrate, sulphate, and organic anions, for example formiate and acetate ion; preferably chloride, bromide, nitrate and acetate anion can be used as anions.

The X-ray powder diffraction patterns of the complexes were determined. The conditions of the X-ray powder diffraction measurements were the following:
Apparatus: Rigaku Corporation, Miniflex II. Powder diffractometer
Radiation: Toshiba A-20, $CuK\alpha_1$ ($\lambda$=1.54059 Å), $CuK\alpha_2$ ($\lambda$=1.54439 Å)
Voltage: 30 kV
Anode current: 15 mA
Accessories: Soller-slit, sample changer
Referent sample: SRRP-432759 silicon powder a=5.430758 Å.
Measurement was steady $\Theta/\Theta$ scan: 4°-50.00° 2$\Theta$.
Step size: 0.02°
Sample: non-powder, measured and stored at room temperature.

It has been surprisingly found that some of the novel complexes are formed in an amorphous form and the other formed in a crystalline form.

Most of the novel complexes were anhydrous, but the calcium chloride complex was crystallised in trihydrate form. The calcium chloride trihydrate complex of vildagliptin has a high melting point (168-174° C.) and is a white powder. The stochiometry of the complex is stable and does not alter during recrystallization.

In most of the novel complexes the molar ration of vildagliptin and the inorganic salt is 1:1 but it has been surprisingly found that zinc chloride is able to form two kinds of complexes, one with a molar ratio being 1:1 and the other with 2:1. The two complexes show significantly different properties. The complex with 1:1 molar ratio has a melting point of 282-286° C. and is a crystalline form. The complex with 2:1 molar ratio has a melting point of °145-149° C. and it has an amorphous form.

In pages 44 to 45 pages of WO 2007019255 it is described that the vildagliptin base completely decomposes in water within three days and only 7.5% active ingredient is detectable after three days contrary to the salts. Under the same reaction conditions, wherein the calcium chloride trihydrate complex of vildagliptin [compound of the general formula III, wherein M denotes calcium(II) ion, A stands for chloride ion, n is 1, x is 1, y is 2 and z is 3] was stirred in water, the relative amount of the non-decomposed active ingredient was 98.7% after 93 hours and 97.6% after 165 hours, which is much more advantageous compared to the vildagliptin base of the formula I.

In case of accelerated (40° C., 75% relative humidity) and standard (25° C., 60% relative humidity) conditions of stability experiments the primary metabolite of the vildagliptin is the 1-[2-(3-hydroxy-adamantane-1-yl-amino)-acetyl]-pyrrolidine-(2S)-carboxamide of the formula VIII, which is formed by the hydrolysis of the nitrile group to acidamide. The hydrolysis takes place rapidly under higher humidity of temperature.

According to our experiments the amount of the metabolite of the formula VIII is increased faster during storage than in the complexes of the present invention. It has been found that the impurity of the formula VIII in vildagliptin base was 43.0% in 0.01 M NaOH solution after 17 hours at room temperature. The impurity of the formula VIII was only 9.5% in the calcium chloride complex of the present invention when stored under the same conditions. A similar process was observed under oxidative conditions (0.3 t % $H_2O_2$ solution, room temperature, 15 minutes) where the amount of the compound of the formula VIII was 48.2% in the vildagliptin base and only 32.2% in the calcium chloride complex of the present invention.

Solid complexes formed by inorganic salts and organic pharmaceutical compounds can not be found among the marketed pharmaceutical compounds.

A further aspect of the present invention is a process for preparing high purity vildagliptin complexes of the formula II which comprises reacting vildagliptin base of the formula I with a suitable metal salt or a hydrate thereof in a suitable organic solvent or in a mixture of suitable organic solvents and water and if desired precipitating the complex with a suitable solvent and separating the formed vildagliptin complex of formula II, and if desired washing the complex with a suitable organic solvent or in a mixture of suitable organic solvents and water and if desired recrystallizing the complex.

A further aspect of the present invention is a process for preparing high purity vildagliptin complexes of formula III which comprises reacting vildagliptin base of formula I with a suitable metal salt or a hydrate thereof in a suitable organic solvent or in a mixture of suitable organic solvents and water and if desired precipitating the complex with suitable solvent and separating the formed vildagliptin complex of formula III and washing the complex with a suitable organic solvent or in a mixture of suitable organic solvents and water if desired and recrystallizing the complex if desired.

A further aspect of the present invention is a process for preparing high purity vildagliptin complexes of formula III which comprises reacting vildagliptin base of formula I with a hydrate of suitable metal salt in a suitable organic solvent and if desired precipitating the complex with suitable solvent and separating the formed vildagliptin complex, I and if desired washing the complex with a suitable organic solvent or in a mixture of suitable organic solvents and water and is desired recrystallizing the complex.

Water, alcohols containing 1 to 4 carbon atoms, acetonitrile or a mixture thereof, preferably ethyl alcohol, 2-propanol or mixture thereof or mixture thereof with water is used as solvent by complex formation.

The metal salt, which is used by the complex formation is applied in an amount of 0.4-3.0 mole(s), preferably 0.45-1.2 mole(s) equivalent calculated on the amount of the vildagliptin, the most preferable amount is 0.95-1.00 mole(s) in case of (1.1) stoichiometric complexes and 0.45-0.50 mole(s) equivalent in case of (2:1) stoichiometric complexes.

Another aspect of the present invention is high purity vildagliptin base of formula I, which is manufactured by using (vildagliptin) complexes of the general formulae II and III. The invention further relates to the high purity vildagliptin salts of the formula IV wherein 'B' stands for a pharmaceutically acceptable organic or inorganic acid anion. The high purity vildagliptin salts of the formula IV can be prepared by using high purity vildagliptin base of the present invention and/or directly by using the (vildagliptin) complexes of the general formulae II and III According to the present specification the term 'high purity' stands for a vildagliptin base, which contains the 3-amino-adamantane-1-ol of the formula V and/or (2S,2'S)-1,1'-{[(3-hydroxytricyklo[3.3.1.1$^{3,7}$]dec-1-yl)imino]bis(1-oxoethane-2,1-diyl)}dipyrrolidine-2-carbonitrile of the formula VII in an amount less than 0.10 w/w %.

The present invention is based on the finding that the high purity vildagliptin base can be preferably prepared by using the novel vildagliptin complexes of the general formulae II and III of the present invention.

The present invention further relates to a process for preparing vildagliptin of the formula I and/or pharmaceutically acceptable salts thereof by using vildagliptin complexes of the formula II or formula III, which comprises reacting the vildagliptin complex of the formula II or the formula III with an inorganic salt or inorganic base in aqueous solution, preferably with alkalimetal carbonate and if desired removing the vildagliptin of the formula I from the aqueous phase by further addition of an inorganic salt, filtering the precipitated products and dissolving the vildagliptin of the formula I from beside the inorganic substances with an organic solvent, filtering the solution and recovering the vildagliptin of the formula I from the filtrated solution and if desired converting it to a salt.

A further aspect of the present invention is a process for preparing vildagliptin of formula I and/or pharmaceutically acceptable salts thereof by using vildagliptin complexes of the formula II or the formula III, which comprises reacting the vildagliptin complex of the formula II or the formula III with an inorganic salt or base, preferably an alkali-metal carbonate dissolved in water and if desired precipitating the vildagliptin of the formula I by further addition of an inorganic salt, extracting the mixture with a suitable organic solvent, such as dichloro methane, separating the phases, drying the organic phase, crystallizing the evaporated and obtained vildagliptin of the formula I and converting it to a salt if desired.

Under the above described conditions compounds of formulae VI and VII, which are the most characteristic impurities of the vildagliptin base, do not form solid complexes. Therefore the complex formation is an excellent method for purifying vildagliptin base and it is more effective than the methods known from the state of the art.

The vildagliptin base of example 7, recovered from the calcium chloride trihydrate complex of vildagliptin according to example 2, has the following properties:

HPLC purity (UV and light scattering method)>99.97% [<0.03% (VII), <0.03% (V), <0.03% (VI)].

Enantiomer purity: (chiral HPLC, UV detection): >99.9%.

If desired the vildagliptin base manufactured according to the above described process can be converted into high purity vildagliptin salts of the general formula IV by using known processes.

It has been surprisingly found that the calcium chloride trihydrate complex of vildagliptin can be compressed significantly more preferably than the vildagliptin base, therefore it possesses more advantageous pharmaceutical properties than the vildagliptin base.

The present invention further relates to a pharmaceutical composition containing vildagliptin complexes of the formula II and/or III and/or high purity vildagliptin of formula I and/or pharmaceutically acceptable salts thereof and one or more known pharmaceutical carriers or excipients.

The pharmaceutical compositions of the present invention contain in general 0.1 to 95.0 percent by weight, preferably 1.0 to 50.0 percent by mass, more preferably 5.0 to 30.0 percent by mass of active ingredient.

The pharmaceutical compositions of the present invention are suitable for oral (e.g. powders, tablets, film-coated tablets, capsules, microcapsules, drops/pills, solutions, suspensions or emulsions), parenteral (e.g. in form of intravenous, intramuscular, subcutaneous or intraperitoneal injections or infusion compositions), rectal (e.g. in form of suppositories), transdermal (e.g. patches) administration, or can be used in the form of implants or for local treatment (e.g. ointment, gels or patches).

The solid, semisolid or liquid pharmaceutical dosage forms of the present invention are known per se, the methods of manufacturing the compositions are known in the state of the art.

The solid pharmaceutical compositions according to the present invention containing the vildagliptin complexes of the formula II and/or III and/or high purity vildagliptin of formula I suitable for oral administration may be powders, capsules, tablets, film-coated tablets, microcapsules etc., optionally comprise binding agents such as gelatine, sorbitol, poly(vinyl-pyrrolidone) etc.; filling agents such as lactose, glucose, starch, calcium phosphate etc.; auxiliary substances for tabletting such as magnesium stearate, talc, polyethylene glycol, silica etc.; wetting agents such as sodium lauryl sulfate etc.

The liquid pharmaceutical compositions containing the vildagliptin complexes of the formula II and/or III and/or high purity vildagliptin of formula I suitable for oral administration may be solutions, suspensions or emulsions and can comprise e.g. suspending agents such as gelatine, carboxymethylcellulose etc.; emulsifiers such as sorbitane monooleate etc.; solvents such as water, oils, glycerol, propyleneglycol, ethanol etc.; preservatives such as methy p-hydroxybenzoate etc. and a the carrier.

Typical parenteral compositions containing the vildagliptin complexes of the formula II and/or III and/or high purity vildagliptin of formula I are liquid pharmaceutical compositions, sterile isotonic solutions, which contains compounds which have influence on pH and preservers beyond the solvent.

Compositions of the present invention for nasal administration containing the vildagliptin complexes of the formula II and/or III and/or high purity vildagliptin of formula I may conveniently be formulated as aerosols, drops, gels and powders.

Semisolid compositions of the present invention containing the vildagliptin complexes of the formula II and/or III and/or high purity vildagliptin of formula I (e.g. suppositories) contain the active ingredient uniformly dispersed in the base, such as polyethylene glycol or cocoa butter.

Another aspect of the present invention is a process for preparing a composition containing vildagliptin complexes of the formula II and/or III and/or high purity vildagliptin of formula I.

The vildagliptin complexes of the formula II and/or III and/or high purity vildagliptin of formula I according to the present invention are manufactured by using known processes. The active ingredient is mixed with solid or liquid pharmaceutical carriers and/or excipients and formulated to galenic form. The dosage forms, carriers, excipients and manufacturing processes listed above as well as other dosage forms, carriers, excipients and manufacturing processes are known per se, see e.g. Remington's Pharmaceutical Sciences, 18$^{th}$ Edition, Mack Publishing Co., Easton, USA (1990).

The compositions containing the vildagliptin complexes of the formula II and/or III and/or vildagliptin of formula I of the present inventions contain the active ingredient in form of dosage units.

The present invention further relates to the use of vildagliptin complexes of formula II and/or III and/or vildagliptin of formula I and/or pharmaceutically acceptable salts thereof as a medicament.

A further aspect of the present invention is the use of vildagliptin complexes of formula II and/or III and/or vildagliptin of formula I according and/or pharmaceutically acceptable salts thereof for the treatment of type 2 diabetes (NIDDM) and the use of vildagliptin complex of the formula II and/or III and/or vildagliptin of formula I and/or pharmaceutically acceptable salts thereof for the manufacture of a medicament for the treatment of type 2 diabetes (NIDDM), which contains of mixing the vildagliptin complexes of formula II and/or III with pharmaceutically acceptable carriers and/or excipients and form to galenic form.

Another aspect of the present invention is a method for prevention and/or treatment of type 2 diabetes (NIDDM), which comprising administering to a patient in need of such treatment a therapeutically effective amount of at least one vildagliptin complex of the formula II and/or III according to claims 2 to 18 and/or vildagliptin of formula I according to claims 25 to 27 and/or a pharmaceutically acceptable salt thereof.

The invention is further elucidated by means of following Examples without limiting the scope of protection to the Examples.

EXAMPLE 1

Process for Preparing Vildagliptin Magnesium(II)-Chloride Complex (2:1)

0.34 g (1.65 mmole) of magnesium(II)-chloride hexahydrate is dissolved in 15 cm$^3$ of 2-propanol at 50° C. under intensive stirring, and 1.0 g (3.3 mmole) of vildagliptin base is added to the solution. The solution is stirred at room temperature for 2 hours and is subsequently evaporated. The remaining crystalline product is washed with propanol and dried.

Yield: 0.90 g (78%) white crystal, amorphous
Melting point: 170-176° C.
Elementary analysis [calculated on the basis of the Formula $C_{17}H_{25}N_3O_2 \cdot \frac{1}{2}MgCl_2$ (351.02)]:

| Calculated: | C: 58.17 | H: 7.18 | Cl: 10.10 | N: 11.97 |
|---|---|---|---|---|
| Measured: | C: 57.96 | H: 7.16 | Cl: 10.15 | N: 11.89 |

Figure 1:
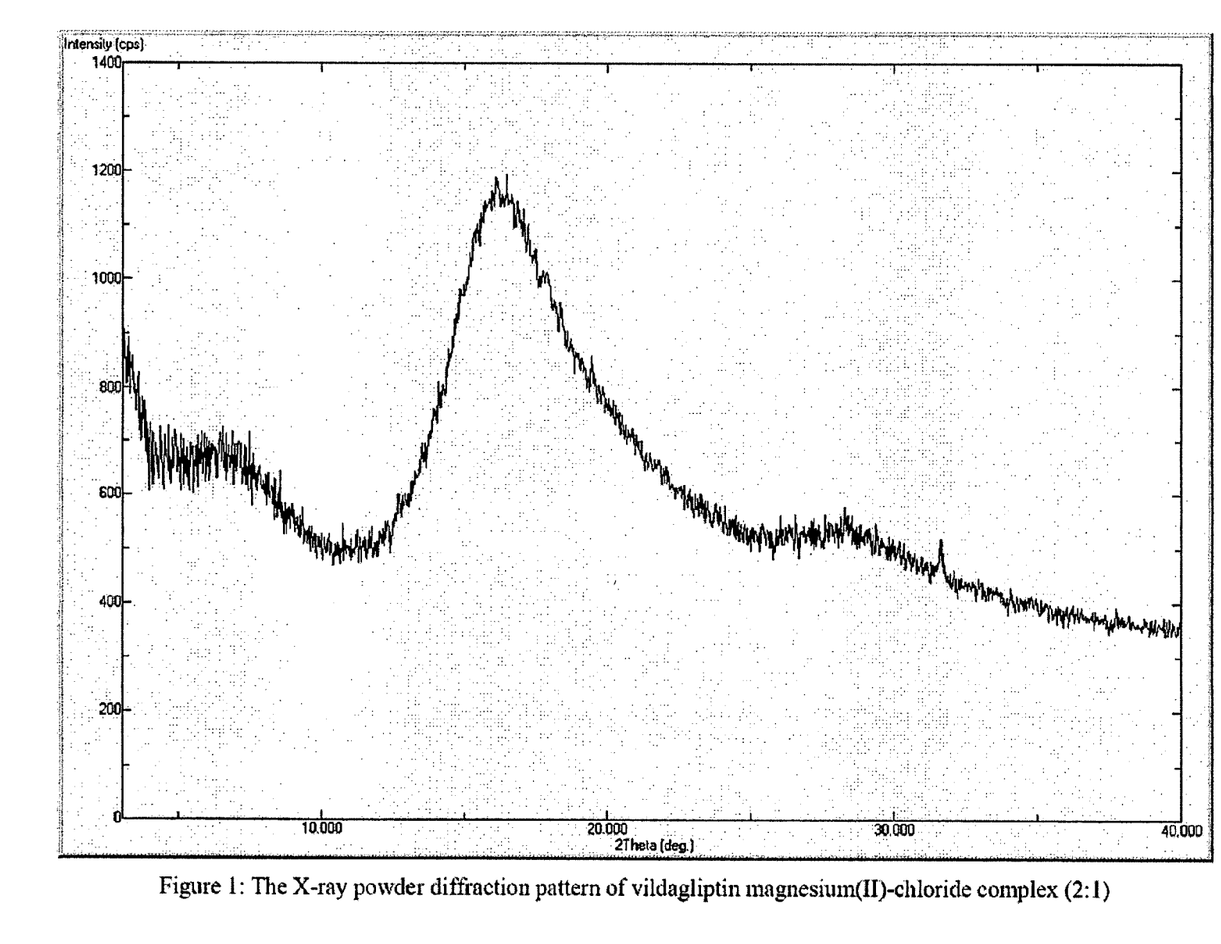
FIG. 1 is an x-ray powder diffraction pattern of vildagliptin magnesium (II)-chloride complex (2:1).

IR (KBr): 3387, 2924, 1638, 1455 cm$^{-1}$.
The X-ray powder diffraction pattern is shown on FIG. 1.

EXAMPLE 2

Process for Preparing Vildagliptin Calcium(II)-Chloride Trihydrate Complex (1:1:3)

A solution of 14.0 g (46.2 mmole) of vildagliptin and 70 cm$^3$ of isopropyl-alcohol is added to a mixture of 6.79 g (46.2 mmole) of $CaCl_2 \cdot 2H_2O$, 14 cm$^3$ of ethanol and 2.5 cm$^3$ of water under intensive stirring at 35-40° C. Crystals are formed while the temperature is continuously decreased to 25° C. and the mixture is stirred for an hour and a half. The precipitated crystals are filtered and washed on the filter with 5 cm$^3$ isopropyl-alcohol. 21.0 g (97%). White product is obtained after drying Melting point: 170-174° C.
$[\alpha]_{D,25} = -56.6°$ (c=1, methanol).
Elementary analysis [calculated on the basis of the Formula $C_{17}H_{25}N_3O_2 \cdot CaCl_2 \cdot 3 H_2O$ (468.44)]:

| Calculaed | C: 43.59 | H: 6.67 | Cl: 15.14 | N: 8.97 |
|---|---|---|---|---|
| Measured | C: 43.46 | H: 6.67 | Cl: 15.22 | N: 8.96 |

IR (KBr): 3381, 3286, 2901, 1628, 1461, 1367, 1338, 1220, 1059, 1035 cm$^{-1}$.

$^1$H-NMR (DMSO-d$_6$, 200 MHz): 5.31 (dd, 1H, J=7.3, 3.7 Hz, 0.2H), 4.73 (dd, 0.8H, J=7.3, 3.7 Hz), 4.54 (m, 1.2H), 3.51 (m, 2.4H), 3.33 (m, 2.4H), 2.12 (m, 7.2H), 1.51 (m, 4.8H), 1.44 (m, 9.6H) ppm.

$^{13}$C-NMR (DMSO-d$_6$, 50 MHz): 170.97, [170.88], [119.85], 119.64, 68.02, [53.26], 53.07, 50.26, [50.15], [46.69], 46.43, [46.10], 45.52, 44.65, [43.94], 43.37, 41.25, [41.17], 35.35, [31.84], 30.48, 29.80, 25.02, [22.74] ppm.

HPLC purity: >99.97% [<0.03% (VII), <0.03% (V), <0.03% (VI)].

Enantiomer purity: >99.9%.

Figure 2:
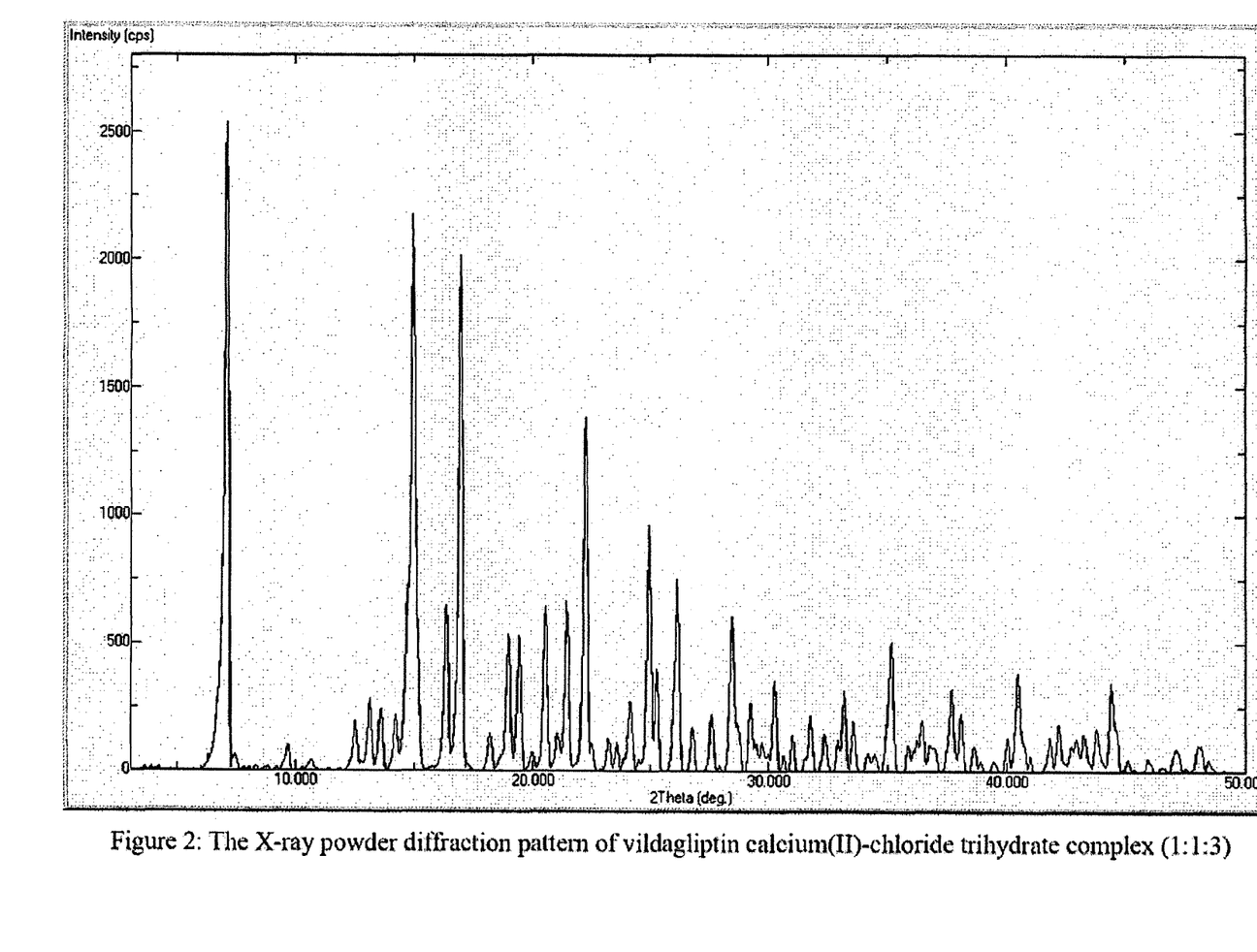
FIG. 2 is an x-ray powder diffraction pattern of vildagliptin calcium (II)-chloride trihydrate complex (1:1:3).

The X-ray powder diffraction pattern is shown on FIG. 2.

X-ray powder diffraction pattern, position of the peaks and relative intensity (>9%) is shown in table 1.

| Peaks | 2 Θ | d (Å) | intensity |
|---|---|---|---|
| 1 | 7.100 | 12.4400 | 100 |
| 2 | 13.160 | 6.7220 | 12 |
| 3 | 13.620 | 6.4960 | 10 |
| 4 | 14.240 | 6.2146 | 9 |
| 5 | 14.720 | 6.0130 | 28 |
| 6 | 14.960 | 5.9170 | 86 |
| 7 | 16.360 | 5.4137 | 26 |
| 8 | 16.980 | 5.2174 | 79 |
| 9 | 19.000 | 4.6670 | 22 |
| 10 | 19.440 | 4.5624 | 21 |
| 11 | 20.540 | 4.3205 | 26 |
| 12 | 21.460 | 4.1373 | 27 |
| 13 | 22.240 | 3.9939 | 55 |
| 14 | 24.140 | 3.6837 | 11 |
| 15 | 24.940 | 3.5673 | 38 |
| 16 | 25.260 | 3.5228 | 16 |
| 17 | 26.140 | 3.4062 | 30 |
| 18 | 27.600 | 3.2292 | 9 |
| 19 | 28.460 | 3.1336 | 24 |
| 20 | 29.240 | 3.0517 | 11 |
| 21 | 30.260 | 2.9512 | 14 |
| 22 | 31.740 | 2.8168 | 9 |
| 23 | 33.140 | 2.7010 | 13 |
| 24 | 35.140 | 2.5517 | 20 |
| 25 | 36.460 | 2.4623 | 8 |
| 26 | 37.700 | 2.3841 | 13 |
| 27 | 38.100 | 2.3600 | 9 |
| 28 | 40.480 | 2.2265 | 16 |
| 29 | 44.420 | 2.0378 | 14 |

EXAMPLE 3

Process for Preparing Vildagliptin Calcium (II)-Chloride Trihydrate Complex (1:1:3)

0.27 g (2.4 mmole) of anhydrous $CaCl_2$ is dissolved in 4 cm$^3$ ethanol and 0.60 g (2.0 mmole) of solid vildagliptin is added to the solution. The solution is heated to 50° C., 0.5 cm$^3$ of water and 15 cm$^3$ of acetonitrile are added and the solution is slowly cooled to room temperature and the mixture is stirred for an hour and a half. The precipitated crystals are filtered and washed with 2×1 cm$^3$ of the solvent mixture, which was used for crystallizing. 0.77 g (1.65 mmole; 83%) of the product is obtained after drying, which shows identical X-ray diffraction pattern to the product according to example 2.

EXAMPLE 4

Process for Preparing Vildagliptin Calcium(II)-Chloride Trihydrate Complex (1:1:3)

A solution of 15.15 g (50.0 mmole) vildagliptin and 95 cm$^3$ of isopropyl-alcohol is added to the mixture of 7.35 g (50.0 mmole) of CaCl$_2$.2H$_2$O, 15 cm$^3$ of ethanol and 3.1 cm$^3$ of water under intensive stirring at 35-40° C. temperature. Crystals are formed while the temperature is continuously decreased to 25° C. and the mixture is stirred for an hour and a half. The precipitated crystals are filtered and washed on the filter with 5 cm$^3$ isopropyl-alcohol. 22.52 g (48.1 mmole; 96.2%) of a white product is obtained after drying, which shows identical X-ray diffraction pattern to the product according to example 2.

EXAMPLE 5

Recrystallization of Vildagliptin Calcium(II)-Chloride Trihydrate Complex (1:1:3)

0.50 g of the product according to example 3 is dissolved in the mixture of 2 cm$^3$ of ethanol and 0.1 cm$^3$ of water while heating, 6 cm$^3$ of acetonitrile are added to the solution and it is slowly cooled to room temperature while stirring for 3 hours. The precipitated crystals are filtered and washed with 1 cm$^3$ of the solvent mixture, which was used for crystallizing and dried in vacuo. 0.39 g (78%) of a white product is obtained, which shows identical X-ray diffraction pattern to the product according to example 2.

EXAMPLE 6

Recrystallization Vildagliptin Calcium(II)-Chloride Trihydrate Complex (1:1:3)

1.0 g (2.14 mmole) of the product according to example 4 is dissolved in 30 cm$^3$ of hot isopropyl-alcohol and the solution is kept at 5° C. for 2 days. The precipitated crystals are filtered, washed with isopropyl-alcohol and dried. 0.56 g (1.20 mmole, 56%) white product is obtained, which shows identical X-ray diffraction pattern to the product according to example 2.

EXAMPLE 7

Process for Preparing Vildagliptin Base Form Vildagliptin Calcium(II)-Chloride Trihydrate (1:1:3) Complex 1.0 g (2.14 mmole) of the product according to example 4 is stirred in 4.0 cm$^3$ of a 10 w/w % sodiumcarbonate solution at 40° C. for 2 minutes. After cooling to room temperature 20 cm$^3$ of dichloromethane and 0.5 g sodium-chloride are added to the solution. After intensive stirring the two-phase system is filtered and the phases are separated.

The aqueous phase is extracted by 20 cm$^3$ of dichloromethane. The collected organic phases are washed with 1 cm$^3$ conc. NaCl, dried over sodium sulphate and evaporated. 0.76 g oil product is obtained which is triturated with 2 cm$^3$ of ethylacetate and the crystalline product is dried in vacuo. Yield: 0.62 g (2.04 mmole; 95%) vildagliptin base Melting point: 149-153° C.

The above product is recrystallized from 10 cm$^3$ of aqueous ethyl acetate containing 1 w/w % water. Yield: 0.48 g white, crystalline product (1.6 mmole; 75% calculated on the basis of the complex)

Melting point: 149-152° C.

HPLC purity: >99.97% [<0.03% (VII), <0.03% (V), <0.03% (VI)].

EXAMPLE 8

Process for Preparing Vildagliptin Base Form Vildagliptin Calcium(II)-Chloride Trihydrate (1:1:3) Complex 1.5 g (3.2 mmole) of the product according to example 4 is stirred in 6.0 cm$^3$ of 10 w/w % sodium carbonate solution at 40° C. for 10 minutes and 1.0 g of sodium chloride is added to the mixture and it is slowly cooled to room temperature while stirring. The mixture is stirred at room temperature for 30 minutes and at 10° C. for further two hours. The precipitated product is filtered, and 1.32 product is obtained after drying. The product is hot stirred with 15 cm$^3$ of aqueous ethyl acetate containing 1 w/w % water for 10 minutes and after filtration the filtrate is slowly cooled. The precipitated crystals are filtered. Yield: 0.63 g (2.08 mmole, 65%) white crystalline product.

Melting product: 149-152° C.

HPLC purity: >99.97% [<0.03% (VII), <0.03% (V), <0.03% (VI)].

EXAMPLE 9

Process for Preparing Vildagliptin Zinc(II)-Chloride Complex (2:1)

0.22 g (1.65 mmole) of zinc(II)-chloride is dissolved in 15 cm$^3$ ethanol at 50° C. under intensive stirring, and 1.0 g (3.3 mmole) of vildagliptin base is added to the solution. The solution is stirred at room temperature for 2 hours. The precipitated crystalline product is filtered, washed with ethyl acetate and dried.

Yield: 1.10 g (90%) white crystal, amorphous

Melting point: 145-149° C.

IR (KBr): 3425, 2922, 1617, 1454, 1417 cm$^{-1}$.

Elementary analysis [calculated on the basis of the Formula C$_{17}$H$_{25}$N$_3$O$_2$.½ZnCl$_2$ (371.55)]:

| | | | | |
|---|---|---|---|---|
| Calculated: | C: 54.96 | H: 6.78 | Cl: 9.54 | N: 11.31 |
| Measured: | C: 54.66 | H: 6.91 | Cl: 9.35 | N: 11.12 |

Figure 3:
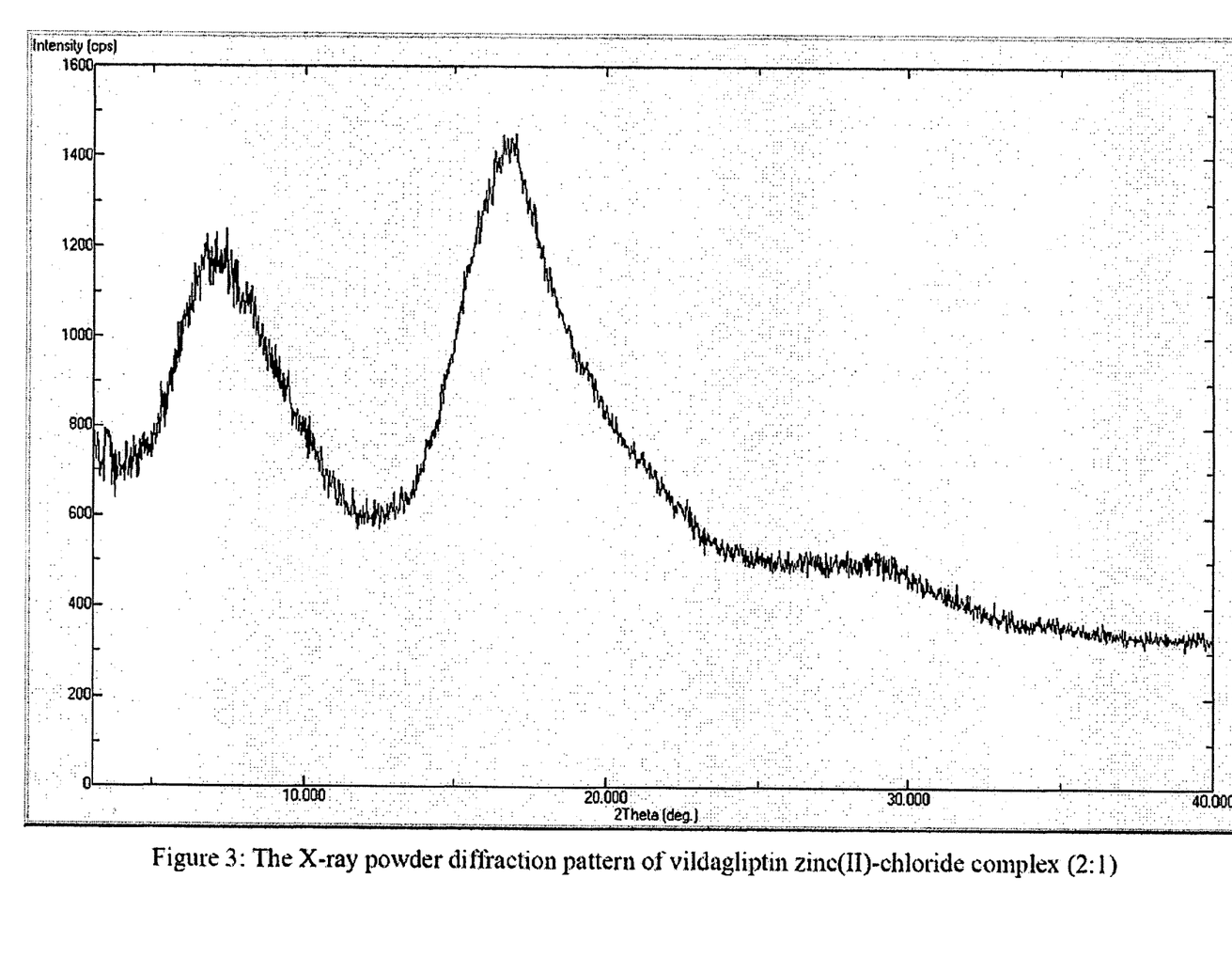
FIG. 3 is an x-ray powder diffraction pattern of vildagliptin zinc (II)-chloride complex (2:1).

The X-ray powder diffraction pattern is shown on FIG. 3.

EXAMPLE 10

Process for Preparing Vildagliptin Zinc(II)-Chloride Complex (1:1)

0.54 g (4.0 mmole) of zinc(II)-chloride is dissolved in 15 cm$^3$ of ethanol at 50° C. under intensive stirring, and 1.0 g (3.3 mmole) of vildagliptin base is added to the solution. The solution is stirred at room temperature for 2 hours. The precipitated crystalline product is filtered, washed with ethanol and dried.

Yield: 1.19 g (82%) white crystal
Melting point: 282-286° C.
IR (KBr): 3419, 2920, 2250, 1600 cm$^{-1}$.
Elementary analysis [calculated on the basis of the Formula $C_{17}H_{25}N_3O_2 \cdot ZnCl_2$ (439.68)]:

| Calculated: | C: 46.44 | H: 5.73 | Cl: 16.13 | N: 9.56 |
|---|---|---|---|---|
| Measured: | C: 46.24 | H: 5.96 | Cl: 16.21 | N: 9.27 |

Figure 4:
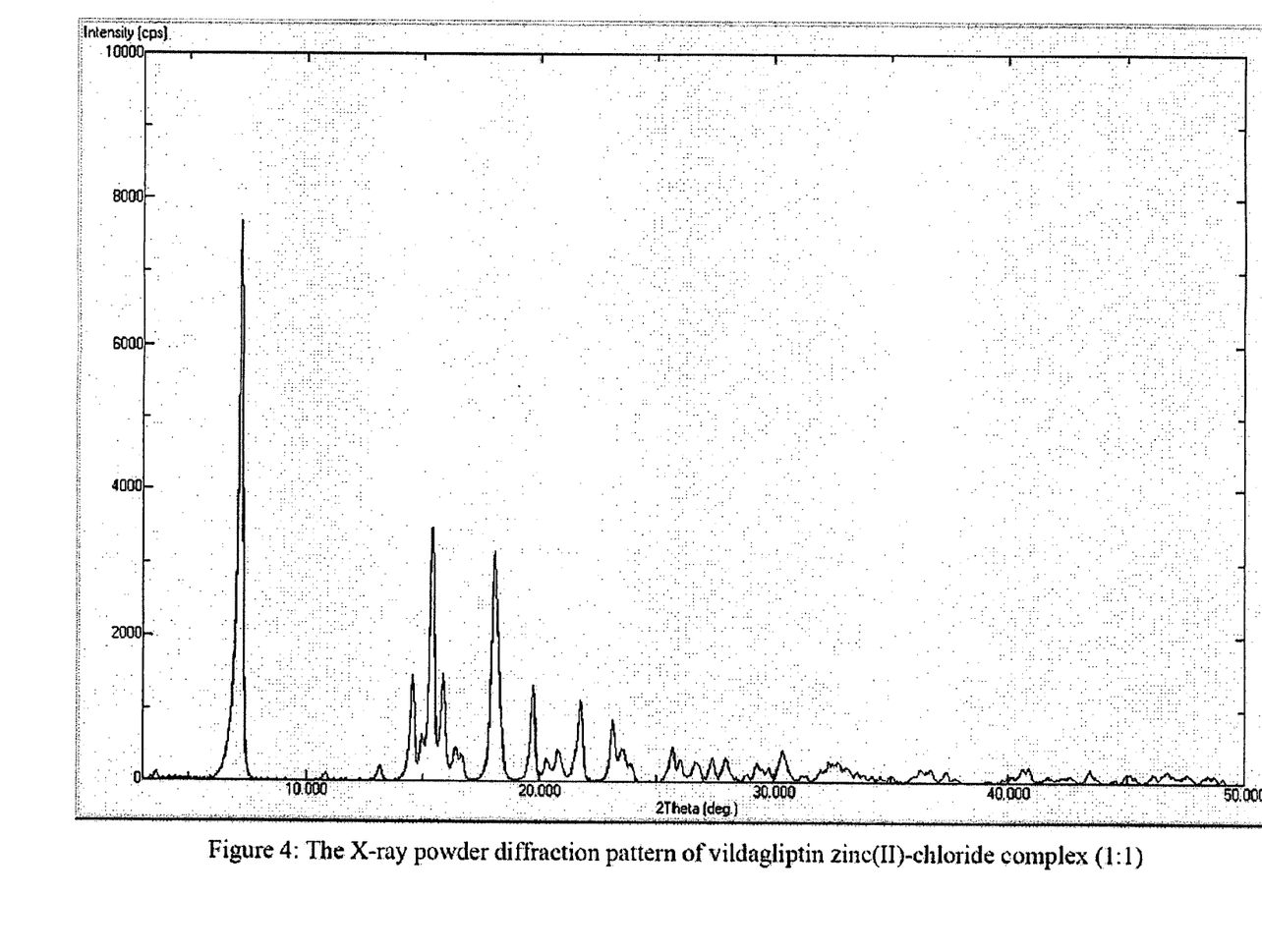
FIG. 4 is an x-ray powder diffraction pattern of Vildagliptin zinc (II)-chloride complex (1:1).

The X-ray powder diffraction pattern is shown on FIG. 4.
X-ray powder diffraction pattern, position of the peaks and relative intensity (>3%) is shown in table 2.

| Peaks | 2 Θ | d (Å) | Intensity |
|---|---|---|---|
| 1 | 7,180 | 12.3016 | 100 |
| 2 | 13,140 | 6.7322 | 4 |
| 3 | 14,560 | 6.0787 | 21 |
| 4 | 15,400 | 5.7490 | 48 |
| 5 | 15,880 | 5.5763 | 21 |
| 6 | 18,100 | 4.8970 | 44 |
| 7 | 19.720 | 4.4982 | 18 |
| 8 | 20,320 | 4.3667 | 5 |
| 9 | 20,820 | 4.2630 | 6 |
| 10 | 21,760 | 4.0809 | 16 |
| 11 | 23,120 | 3.8438 | 12 |
| 12 | 23,560 | 3.7730 | 7 |
| 13 | 25,640 | 3.4715 | 7 |
| 14 | 26,700 | 3.3360 | 4 |
| 15 | 27,340 | 3.2594 | 5 |
| 16 | 27,920 | 3.1929 | 5 |
| 17 | 29,280 | 3.0477 | 4 |
| 18 | 30,360 | 2.9417 | 7 |
| 19 | 32,000 | 2.7945 | 3 |
| 20 | 32,380 | 2.7626 | 4 |
| 21 | 32,700 | 2.7363 | 4 |
| 22 | 33,120 | 2.7026 | 3 |
| 23 | 36,280 | 2.4741 | 3 |
| 24 | 36,680 | 2.4480 | 3 |
| 25 | 37,340 | 2.4062 | 3 |
| 26 | 40,800 | 2.2098 | 3 |
| 27 | 43,400 | 2.0833 | 3 |
| 28 | 46,700 | 1.9435 | 3 |

EXAMPLE 11

Process for Preparing Vildagliptin Copper (II)-Chloride Complex (1:1)

0.68 g (4.0 mmole) of copper(II)-chloride is dissolved in 15 cm$^3$ of ethanol at 50° C. under intensive stirring, and 1.0 g (3.3 mmole) of vildagliptin base is added to the solution. The solution is stirred at room temperature for 2 hours and 10 cm$^3$ of diisopropyl ether are added to the mixture. The precipitated crystalline product is filtered, washed with diisopropyl ether and dried.

Yield: 1.40 g (97%) brown crystal, amorphous
Melting point: 146-150° C.
IR (KBr): 3424, 2925, 2250, 1599 cm$^{-1}$.
Elementary analysis [calculated on the basis of the Formula $C_{17}H_{25}N_3O_2 \cdot CuCl_2$ (437.86)]

| Calculated: | C: 46.63 | H: 5.76 | Cl: 16.19 | N: 9.60 |
|---|---|---|---|---|
| Measured: | C: 46.31 | H: 5.92 | Cl: 16.25 | N: 9.37 |

Figure 5:
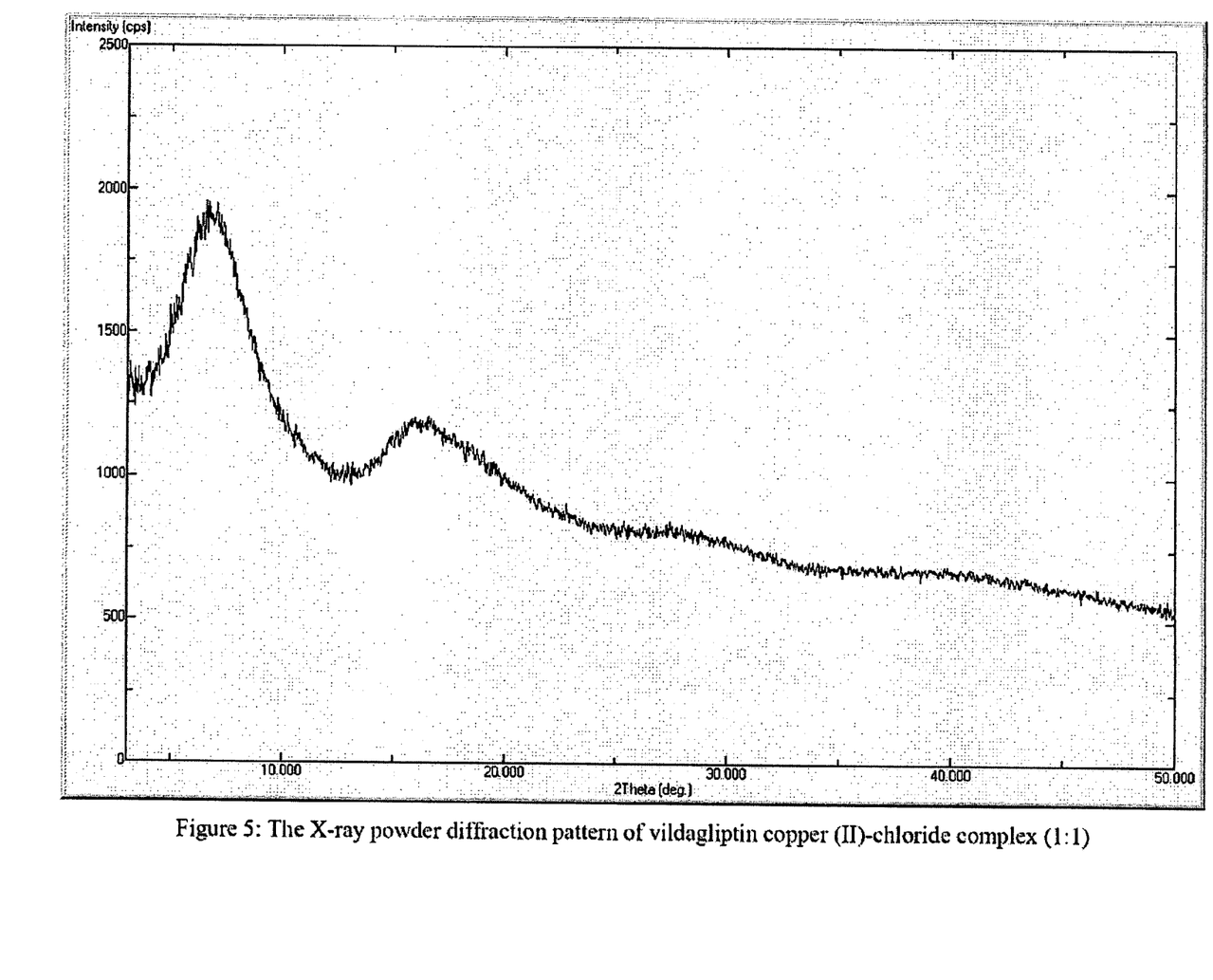
FIG. 5 is an x-ray powder diffraction pattern of vildagliptin copper (II)-chloride complex (1:1).

The X-ray powder diffraction pattern is shown on FIG. 5.

EXAMPLE 12

Process for Preparing Vildagliptin Zinc(II)-Bromide Complex (1:1)

0.90 g (4.0 mmole) of zinc(II)-bromide is dissolved in 15 cm$^3$ of ethanol at 50° C. under intensive stirring, and 1.0 g (3.3 mmole) of vildagliptin base is added to the solution. The solution is stirred at room temperature for 2 hours. The precipitated crystalline product is filtered, washed with ethanol and dried.

Yield: 1.49 g (85%) white crystal.
Melting point: 287-291° C.
IR (KBr): 3471, 3197, 1605, 1456, 1024 cm$^{-1}$.
Elementary analysis [calculated on the basis of the Formula $C_{17}H_{25}N_3O_2 \cdot ZnBr_2$ (528.59)]:

| Calculated: | C: 38.63 | H: 4.77 | Br: 30.23 | N: 7.95 |
|---|---|---|---|---|
| Measured: | C: 38.50 | H: 4.80 | Br: 29.98 | N: 7.84 |

Figure 6:
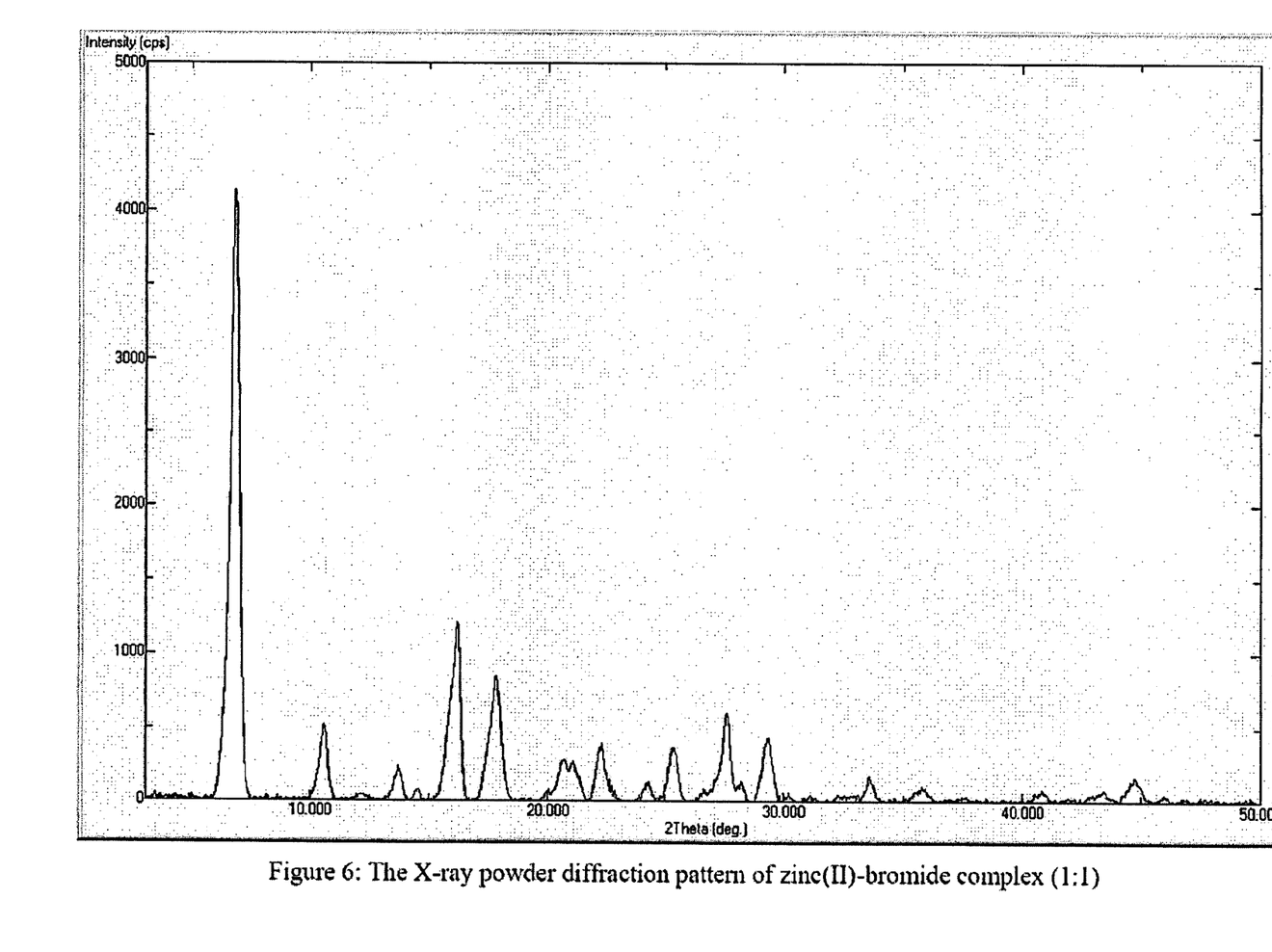
FIG. 6 is an x-ray powder diffraction pattern of vildagliptin zinc (II)-bromide complex (1:1).

The X-ray powder diffraction pattern is shown on FIG. 6.
X-ray powder diffraction pattern, position of the peaks and relative intensity (>3%) is shown in table 3.

| Peak | 2 Θ | d (Å) | Intensity |
|---|---|---|---|
| 1 | 6,800 | 12.9882 | 100 |
| 2 | 10,560 | 8.3705 | 13 |
| 3 | 13,700 | 6.4583 | 6 |
| 4 | 16,100 | 5.5005 | 25 |
| 5 | 17,800 | 4.9789 | 21 |
| 6 | 20,800 | 4.2670 | 7 |
| 7 | 22,260 | 3.9904 | 10 |
| 8 | 24,200 | 3.6747 | 4 |
| 9 | 25,320 | 3.5146 | 9 |
| 10 | 27,540 | 3.2361 | 15 |
| 11 | 29,300 | 3.0456 | 11 |
| 12 | 33,600 | 2.6650 | 4 |
| 13 | 35,760 | 2.5089 | 3 |
| 14 | 44,740 | 2.0239 | 4 |

EXAMPLE 13

Process for Preparing Vildagliptin Zinc(II)-Acetate Complex (1:1)

0.88 g (4.0 mmole) of zinc(II)-acetate dihydrate is dissolved in 15 cm$^3$ of ethanol at 50° C. under intensive stirring, and 1.0 g (3.3 mmole) of vildagliptin base is added to the solution. The solution is stirred at room temperature for 2 hours and evaporated in vacuo. The residual oily product is triturated with diisopropyl ether, the crystalline product obtained is filtered, washed with diisopropyl ether and dried.

Yield: 1.48 g (92%) light yellow crystal, amorphous
Melting point: 108-111° C.
IR (KBr): 3407, 2924, 2247, 1618, 1420 cm$^{-1}$.
Elementary analysis [calculated on the basis of the Formula $C_{17}H_{25}N_3O_2 \cdot Zn(CH_3COO)_2$ (486.87)]:

| Calculated: | C: 51.81 | H: 6.42 | N: 8.63 |
|---|---|---|---|
| Measured: | C: 51.53 | H: 4.70 | N: 8.53 |

Figure 7:
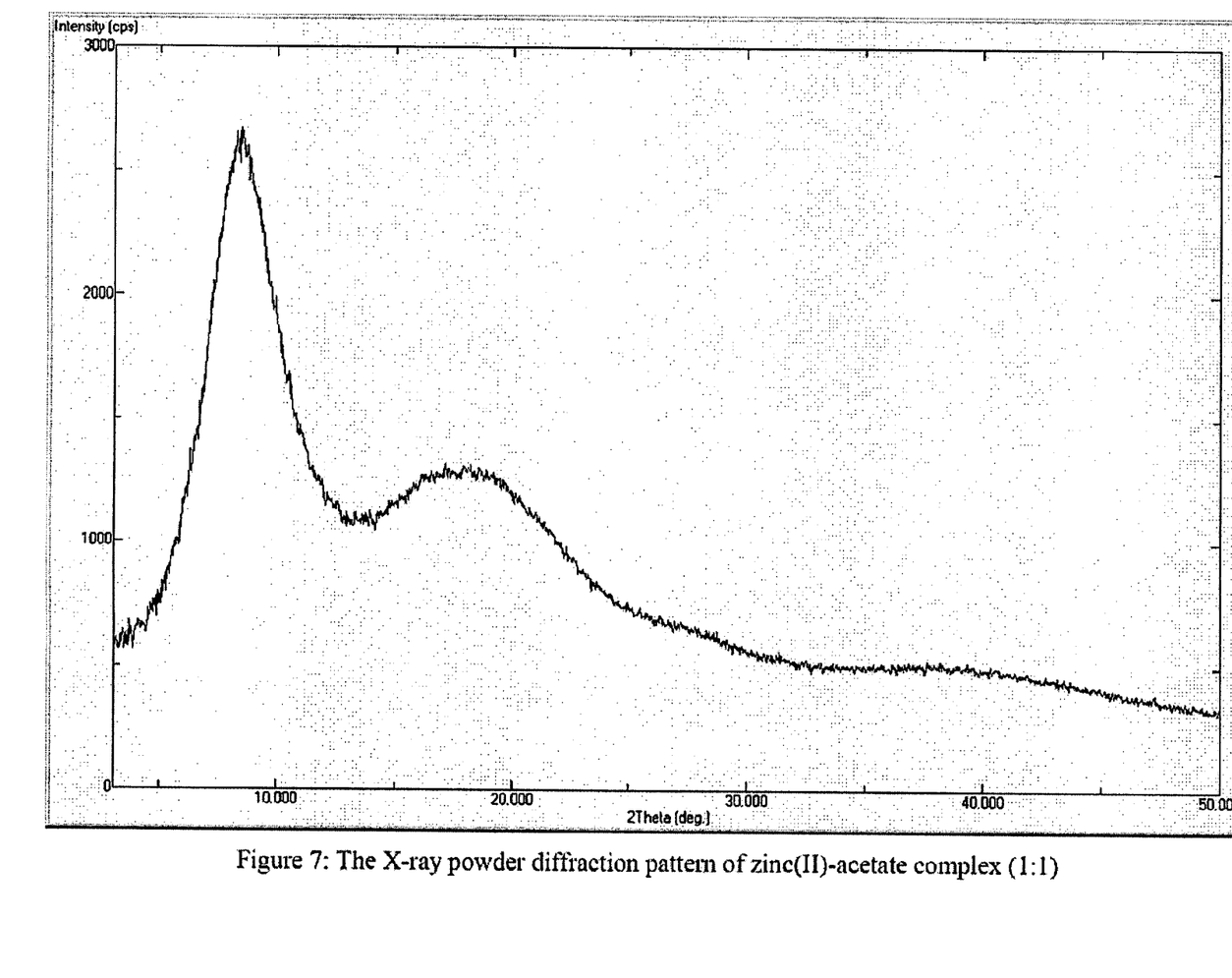
FIG. 7 is an x-ray powder diffraction pattern of vildagliptin zinc (II)-acetate complex (1:1).

The X-ray powder diffraction pattern is shown on FIG. 7.

EXAMPLE 14

Process for Preparing Vildagliptin Stroncium(II)-Nitrate Complex (1:1)

0.85 g (4.0 mmole) of stroncium(II)-nitrate is dissolved in 15 cm³ of ethanol at 50° C. under intensive stirring, and 1.0 g (3.3 mmole) of vildagliptin base is added to the solution. The solution is stirred at room temperature for 2 hours. The precipitated crystalline product is filtered, washed with ethanol and dried.

Yield: 1.30 g (77%) white crystal.
Melting point: 151-155° C.
IR (KBr): 3294, 2238, 1657, 1406, 1354, 1310 cm$^{-1}$.
Elementary analysis [calculated on the basis of the Formula $C_{17}H_{25}N_3O_2 \cdot Sr(NO_3)_2$ (515.04)]:

| | | | |
|---|---|---|---|
| Calculated: | C: 39.65 | H: 4.89 | N: 13.60 |
| Measured: | C: 39.29 | H: 4.65 | N: 13.41 |

Figure 8:
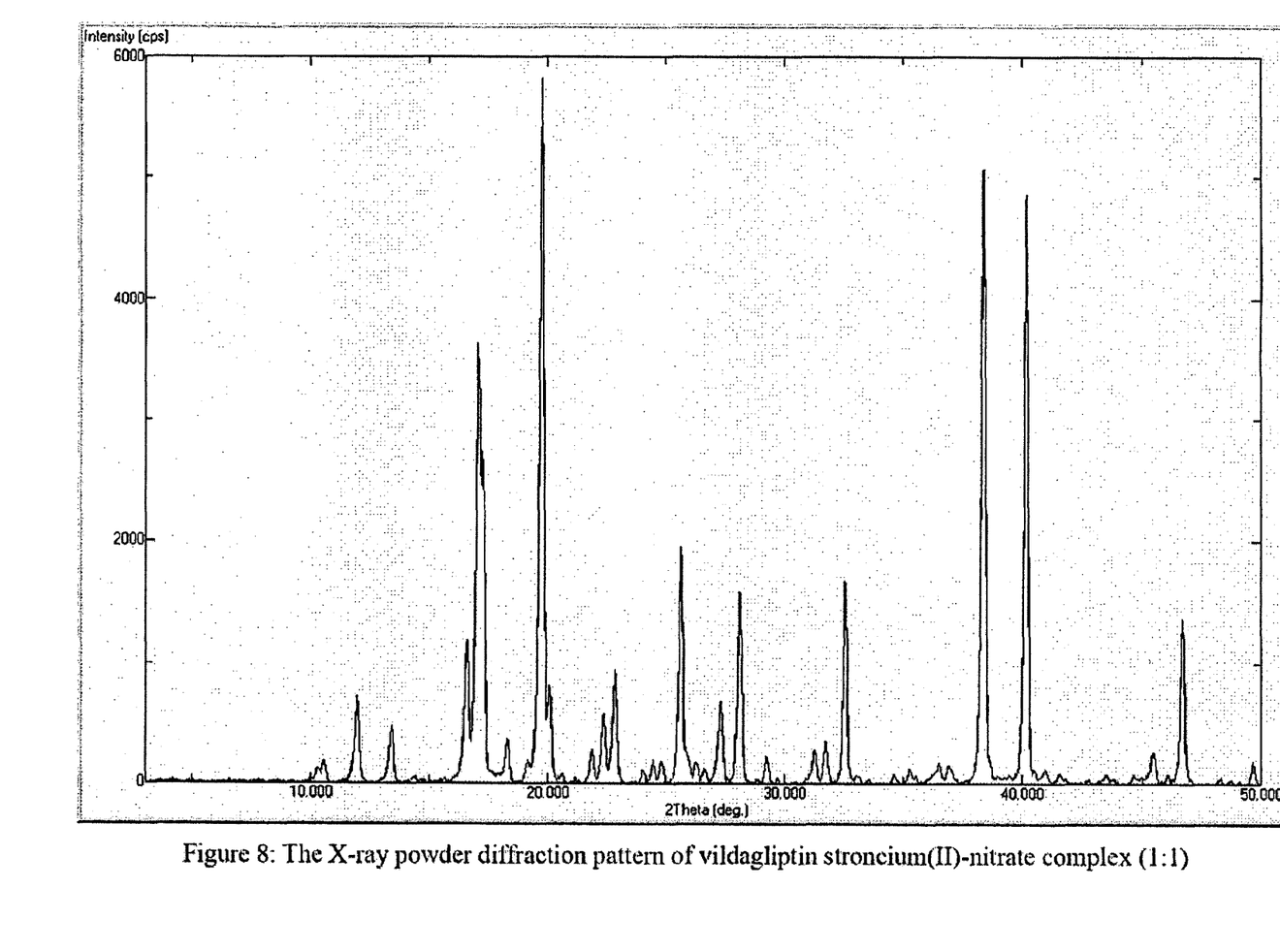
FIG. 8 is an x-ray powder diffraction pattern of vildagliptin strontium (II)-nitrate complex (1:1).

The X-ray powder diffraction pattern is shown on FIG. 8. X-ray powder diffraction pattern, position of the peaks and relative intensity (>4%) is shown in table 4.

| Peak | 2 Θ | d (Å) | Intensity |
|---|---|---|---|
| 1 | 10,560 | 8.3705 | 4 |
| 2 | 11,960 | 7.3937 | 13 |
| 3 | 13,420 | 6.5924 | 9 |
| 4 | 16,580 | 5.3424 | 20 |
| 5 | 17,140 | 5.1691 | 57 |
| 6 | 18,320 | 4.8387 | 7 |
| 7 | 19,780 | 4.4847 | 100 |
| 8 | 21,880 | 4.0588 | 5 |
| 9 | 22,380 | 3.9692 | 10 |
| 10 | 22,860 | 3.8870 | 17 |
| 11 | 24,820 | 3.5843 | 4 |
| 12 | 25,620 | 3.4741 | 33 |
| 13 | 27,300 | 3.2640 | 12 |
| 14 | 28,100 | 3.1729 | 28 |
| 15 | 29,240 | 3.0517 | 4 |
| 16 | 31,260 | 2.8590 | 5 |
| 17 | 31,740 | 2.8168 | 7 |
| 18 | 32,560 | 2.7477 | 29 |
| 19 | 36,480 | 2.4610 | 3 |
| 20 | 38,380 | 2.3434 | 88 |
| 21 | 40,180 | 2.2425 | 84 |
| 22 | 45,440 | 1.9944 | 5 |
| 23 | 46,700 | 1.9435 | 24 |

The invention claimed is:

1. A 1-[2-(3-hydroxyadamant-1-yl-amino)acetyl]pyrrolidin-(2S)-carbonitrile (vildagliptin) complex of the Formula II (II)

wherein
M is an alkali metal, alkaline earth metal or transitional metal cation
A is an organic or inorganic anion
n is 1 or 2
x and y are each 1, 2 or 3
or an amorphous or crystalline form thereof.

2. Vildagliptin magnesium-chloride complex (2:1) of the Formula II according to claim 1, wherein M is a magnesium (II) ion, A is a chloride ion, n is 2, x is 1, y is 2.

3. Vildagliptin copper-chloride complex (1:1) of the Formula II according to claim 1, wherein M is a copper(II) ion, A is a chloride ion, n is 1, x is 1, y is 2.

4. Vildagliptin zinc-chloride complex (1:1) of the Formula II according to claim 1, wherein M is a zinc(II) ion, A is a chloride ion, n is 1, x is 1, y is 2.

5. Vildagliptin zinc-chloride complex (1:1) according to claim 4, which shows an X-ray powder diffraction pattern having characteristic peaks at reflection angle 2 T (±0.2° 2 T) of about 7,180; 15,400; 18,100 taken with a powder diffractometer with radiation Toshiba A-20, CuKα$_1$ (λ=1.54059 Angstroms), CuKα$_2$ (λ=1.54439 Angstroms).

6. Vildagliptin zinc-chloride complex (1:1) according to claim 5, which shows an X-ray powder diffraction pattern according to the following table

| 2 Θ | d (Å) | Relative intensity (%) |
|---|---|---|
| 7.180 | 12.3016 | 100 |
| 13.140 | 6.7322 | 4 |
| 14.560 | 6.0787 | 21 |
| 15.400 | 5.7490 | 48 |
| 15.880 | 5.5763 | 21 |
| 18.100 | 4.8970 | 44 |
| 19.720 | 4.4982 | 18 |
| 20.320 | 4.3667 | 5 |
| 20.820 | 4.2630 | 6 |
| 21.760 | 4.0809 | 16 |
| 23.120 | 3.8438 | 12 |
| 23.560 | 3.7730 | 7 |
| 25.640 | 3.4715 | 7 |
| 26.700 | 3.3360 | 4 |
| 27.340 | 3.2594 | 5 |
| 27.920 | 3.1929 | 5 |
| 29.280 | 3.0477 | 4 |
| 30.360 | 2.9417 | 7 |
| 32.000 | 2.7945 | 3 |
| 32.380 | 2.7626 | 4 |
| 32.700 | 2.7363 | 4 |
| 33.120 | 2.7026 | 3 |
| 36.280 | 2.4741 | 3 |
| 36.680 | 2.4480 | 3 |
| 37.340 | 2.4062 | 3 |
| 40.800 | 2.2098 | 3 |
| 43.400 | 2.0833 | 3 |
| 46.700 | 1.9435 | 3. |

7. Vildagliptin zinc-bromide complex (1:1) of formula II according to claim 1, wherein M is a zinc(II) ion, A is a bromide ion, n is 1, x is 1, y is 2.

8. Vildagliptin zinc-bromide complex (1:1) according to claim 7, which shows an X-ray powder diffraction pattern having characteristic peaks at reflection angle 2 T (±0.2° 2 T) of about 6,800; 16,100 taken with a powder diffractometer with radiation Toshiba A-20, CuKα$_1$ (λ=1.54059 Angstroms), CuKα$_2$ (λ=1.54439 Angstroms).

9. Vildagliptin zinc-bromide complex (1:1) according to claim 8, which shows an X-ray powder diffraction pattern according to the following table

| 2 Θ | d (Å) | Relative intensity (%) |
|---|---|---|
| 6.800 | 12.9882 | 100 |
| 10.560 | 8.3705 | 13 |
| 13.700 | 6.4583 | 6 |
| 16.100 | 5.5005 | 25 |
| 17.800 | 4.9789 | 21 |
| 20.800 | 4.2670 | 7 |

| 2 Θ | d (Å) | Relative intensity (%) |
|---|---|---|
| 22.260 | 3.9904 | 10 |
| 24.200 | 3.6747 | 4 |
| 25.320 | 3.5146 | 9 |
| 27.540 | 3.2361 | 15 |
| 29.300 | 3.0456 | 11 |
| 33.600 | 2.6650 | 4 |
| 35.760 | 2.5089 | 3 |
| 44.740 | 2.0239 | 4. |

10. Vildagliptin zinc-acetate complex (1:1) of formula II according to claim 1, wherein M is a zinc(II) ion, A is an acetate anion, n is 1, x is 1, y is 2.

11. Vildagliptin strontium-nitrate complex (1:1) of formula II according to claim 1, wherein M denotes strontium (II) ion, A is a nitrate anion, n is 1, x is 1, y is 2.

12. Vildagliptin strontium-nitrate complex (1:1) according to claim 11, which shows an X-ray diffraction pattern having characteristic peaks at reflection angle 2 T (±0.2 ° 2 T) of about 19.780; 38.380; 40.180 taken with a powder diffractometer with radiation Toshiba A-20, CuKα$_1$ (λ=1.54059 Angstroms), CuKα2 (λ=1.54439 Angstroms).

13. Vildagliptin strontium-nitrate complex (1:1) according to claim 12 which shows an X-ray powder diffraction pattern according to the following table

| 2 Θ | d (Å) | Relative intensity (%) |
|---|---|---|
| 10.560 | 8.3705 | 4 |
| 11.960 | 7.3937 | 13 |
| 13.420 | 6.5924 | 9 |
| 16.580 | 5.3424 | 20 |
| 17.140 | 5.1691 | 57 |
| 18.320 | 4.8387 | 7 |
| 19.780 | 4.4847 | 100 |
| 21.880 | 4.0588 | 5 |
| 22.380 | 3.9692 | 10 |
| 22.860 | 3.8870 | 17 |
| 24.820 | 3.5843 | 4 |
| 25.620 | 3.4741 | 33 |
| 27.300 | 3.2640 | 12 |
| 28.100 | 3.1729 | 28 |
| 29.240 | 3.0517 | 4 |
| 31.260 | 2.8590 | 5 |
| 31.740 | 2.8168 | 7 |
| 32.560 | 2.7477 | 29 |
| 36.480 | 2.4610 | 3 |
| 38.380 | 2.3434 | 88 |
| 40.180 | 2.2425 | 84 |
| 45.440 | 1.9944 | 5 |
| 46.700 | 1.9435 | 24. |

14. A pharmaceutical composition containing a vildagliptin complex of the Formula II according to claim 1 or a pharmaceutically acceptable salt thereof and a pharmaceutical excipient.

15. A 1-[2-(3-hydroxyadamant-1-yl-amino)acetyl]pyrrolidin-(2S)-carbonitrile (vildagliptin) complex containing stoichiometric or non-stoichiometric water of the Formula (III)

(III)

wherin

M is an alkali metal, alkaline earth metal or transitional metal cation

A is an organic or inorganic anion n is 1 or 2 x and y are each 1, 2, or 3 z is a number between 0.5 to 4 or an amorphous or crystalline form thereof.

16. Vildagliptin calcium-chloride trihydrate complex (1:1:3) of the Formula III according to claim 15, wherein M is a calcium(II) ion, A is a chloride ion, n is 1, x is 1, y is 2 and z is 3.

17. Vildagliptin calcium-chloride trihydrate complex according to claim 16, which shows an X-ray powder diffraction pattern having characteristic peaks at reflection angle 2 T (±0.2° 2 T) of about 7, 100; 14,960; 16,980taken with a powder diffractometer with radiation Toshiba A-20, CuKα$_1$ (λ=1.54059 Angstroms), CuKα$_2$ (λ=1.54439 Angstroms).

18. Vildagliptin calcium-chloride trihydrate complex according to claim 17, which shows an X-ray powder diffraction pattern according to the following table

| 2 Θ | d (Å) | Relative intensity (%) |
|---|---|---|
| 7.100 | 12.4400 | 100 |
| 13.160 | 6.7220 | 12 |
| 13.620 | 6.4960 | 10 |
| 14.240 | 6.2146 | 9 |
| 14.720 | 6.0130 | 28 |
| 14.960 | 5.9170 | 86 |
| 16.360 | 5.4137 | 26 |
| 16.980 | 5.2174 | 79 |
| 19.000 | 4.6670 | 22 |
| 19.440 | 4.5624 | 21 |
| 20.540 | 4.3205 | 26 |
| 21.460 | 4.1373 | 27 |
| 22.240 | 3.9939 | 55 |
| 24.140 | 3.6837 | 11 |
| 24.940 | 3.5673 | 38 |
| 25.260 | 3.5228 | 16 |
| 26.140 | 3.4062 | 30 |
| 27.600 | 3.2292 | 9 |
| 28.460 | 3.1336 | 24 |
| 29.240 | 3.0517 | 11 |
| 30.260 | 2.9512 | 14 |
| 31.740 | 2.8168 | 9 |
| 33.140 | 2.7010 | 13 |
| 35.140 | 2.5517 | 20 |
| 36.460 | 2.4623 | 8 |
| 37.700 | 2.3841 | 13 |
| 38.100 | 2.3600 | 9 |
| 40.480 | 2.2265 | 16 |
| 44.420 | 2.0378 | 14. |

19. A pharmaceutical composition containing a vildagliptin complex of the Formula III according to claim 15 or a pharmaceutically acceptable salt thereof and a pharmaceutical excipient.

20. A process for preparing high purity vildagliptin complexes of Formula (II) according to claim 1 which comprises the steps of reacting vildagliptin base with a metal salt or a hydrate thereof in an organic solvent or in a mixture of organic solvents and water and separating the formed vildagliptin complex.

21. The process according to claim 20, which comprises using the metal salt in an amount of 0.4 to 3 mol equivalent.

22. The process according to claim 20, wherein the solvent is water, alcohol containing 1 to 4 carbon atoms, acetonitrile or a mixture thereof.

23. A process for preparing vildagliptin or a pharmaceutically acceptable salt thereof using a vildagliptin complex of the Formula (II) as defined in claim 1, which comprises the steps of reacting the vildagliptin complex of the Formula (II) with an inorganic salt, and if desired precipitating the vildagliptin by further addition of an inorganic salt, filtering the precipitated compounds and separating the vildagliptin from the inorganic salts by dissolving in an organic solvent, filtering the solution and recovering the vildagliptin from the filtrated solution and if desired converting the vildagliptin to a salt.

24. A process for preparing vildagliptin or a pharmaceutically acceptable salt thereof using a vildagliptin complex of the Formula (II) as defined in claim 1, which comprises the steps of reacting the vildagliptin complex of the Formula (II) with an inorganic salt, and if desired precipitating the vildagliptin by further addition of an inorganic salt, extracting the mixture with suitable organic solvent, separating the phases, drying the organic phase, crystallizing the obtained vildagliptin and converting the vildagliptin to a salt if required.

25. A process for preparing high purity vildagliptin complexes of the Formula (III) according to claim 15 containing a stoichiometric amount of water, which comprises the steps of reacting the vildagliptin base with a suitable metal salt or a hydrate thereof in a solvent selected from water, alcohol containing 1 to 4 carbon atoms, acetonitrile or a mixture thereof to introduce water of hydration into the formed vildagliptin complex and separating the formed vildagliptin complex.

26. The process according to claim 25, which comprises using the metal salt in an amount of 0.9 to 1.3 mol equivalent.

27. A process for preparing vildagliptin or a pharmaceutically acceptable salt thereof using a vildagliptin complex of the Formula (III) as defined in claim 15, which comprises the steps of reacting the vildagliptin complex of the Formula (III) with an inorganic salt and if desired precipitating the vildagliptin of the formula I by further addition of an inorganic salt, filtering the precipitated compounds and separating the vildagliptin from the inorganic salts by dissolving in an organic solvent, filtering the solution and recovering the vildagliptin from the filtrated solution and if desired converting the vildagliptin to a salt.

28. A process for preparing vildagliptin or a pharmaceutically acceptable salt thereof using a vildagliptin complex of the Formula (III) as defined in claim 15, which comprises the steps of reacting the vildagliptin complex of the Formula (III) with an inorganic salt, and if desired precipitating the vildagliptin by further addition of an inorganic salt, extracting the mixture with a suitable organic solvent, separating the phases, drying the organic phase, crystallizing the obtained vildagliptin and converting the vildagliptin to a salt if required.

29. A process for treating type 2 diabetes (NIDDM), which comprises the step of administering to a patient in need of such treatment a therapeutically effective amount of at least one vildagliptin complex of the Formula II as defined in claim 1 or a pharmaceutically acceptable salt thereof.

30. A process for treating type 1 diabetes (NIDDM), which comprises the step of administering to a patient in need of such treatment a therapeutically effective amount of at least one vildagliptin complex of the Formula III as defined in claim 3 or a pharmaceutically acceptable salt thereof.

\* \* \* \* \*